US00PP32652P2

(12) United States Plant Patent
Barnes

(10) Patent No.: US PP32,652 P2
(45) Date of Patent: Dec. 15, 2020

(54) ***CALIBRACHOA* PLANT NAMED 'BBCAL83901'**

(50) Latin Name: ***Calibrachoa* sp.**
Varietal Denomination: BBCAL83901

(71) Applicant: Brent D. Barnes, Riverside, CA (US)

(72) Inventor: Brent D. Barnes, Riverside, CA (US)

(73) Assignee: PLANT 21 LLC, Bonsall, CA (US)

( * ) Notice: Subject to any disclaimer, the term of this patent is extended or adjusted under 35 U.S.C. 154(b) by 0 days.

(21) Appl. No.: 16/873,487

(22) Filed: Apr. 17, 2020

(30) Foreign Application Priority Data

May 17, 2019 (CA) ..... PBR 19-9873

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC ... A01H 5/02; A01H 5/12; A01H 5/00; A01H 6/82; A01H 6/821; A01H 6/14
See application file for complete search history.

*Primary Examiner* — June Hwu
(74) *Attorney, Agent, or Firm* — C. Anne Whealy

(57) ABSTRACT

A new and distinct *Calibrachoa* plant named 'BBCAL83901', characterized by its compact, upright to outwardly spreading and mounding plant habit; moderately vigorous growth habit; freely branching habit; dense and bushy appearance; early and freely flowering habit; dark red-colored flowers with bright yellow-colored throats; and good garden performance.

1 Drawing Sheet

Botanical designation: *Calibrachoa* sp.
Cultivar denomination: 'BBCAL83901'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9873. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Calibrachoa* plant, botanically known as *Calibrachoa* sp. and hereinafter referred to by the name 'BBCAL83901'.

The new *Calibrachoa* plant is a product of a planned breeding program conducted by the Inventor in Bonsall, Calif. The objective of the breeding program is to create new compact, uniform, freely-branching and freely-flowering

*Calibrachoa* plants with unique and attractive flower colors and patterns and good garden performance.

The new *Calibrachoa* plant originated from a cross-pollination conducted by the Inventor in Bonsall, Calif. on Sep. 17, 2015 of a proprietary seedling selection of *Calibrachoa* sp. identified as code number 15CB354-01, not patented, as the female, or seed, parent with *Calibrachoa* sp. 'Unique Light Red', not patented, as the male, or pollen, parent. The new *Calibrachoa* plant was discovered and first selected by the Inventor as a single flowering plant within the progeny of the stated cross-pollination in a controlled greenhouse environment in Bonsall, Calif. on Jun. 22, 2016.

Asexual reproduction of the new *Calibrachoa* plant by vegetative terminal cuttings in a controlled greenhouse environment in Bonsall, Calif. since Jun. 25, 2016 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBCAL83901'. These characteristics in combination distinguish 'BBCAL83901' as a new and distinct *Calibrachoa* plant:

1. Compact, upright to outwardly spreading and mounding plant habit.

2. Moderately vigorous growth habit.
3. Freely branching habit; dense and bushy appearance.
4. Early and freely flowering habit.
5. Dark red-colored flowers with bright yellow-colored throats.
6. Good garden performance.

Plants of the new *Calibrachoa* differ primarily from plants of the female parent selection in the following characteristics:

1. Plants of the new *Calibrachoa* are more freely flowering than plants of the female parent selection.
2. Plants of the new *Calibrachoa* flower earlier than plants of the female parent selection.
3. Plants of the new *Calibrachoa* and the female parent selection differ in flower color as flowers of plants of the new *Calibrachoa* are dark red in color whereas flowers of plants of the female parent selection are cherry red in color.

Plants of the new *Calibrachoa* differ primarily from plants of the male parent, 'Unique Light Red', in the following characteristics:

1. Plants of the new *Calibrachoa* are more mounding than and not as trailing as plants of 'Unique Light Red'.
2. Plants of the new *Calibrachoa* and 'Unique Light Red' differ in flower color as flowers of plants of the new *Calibrachoa* are dark red in color whereas flowers of plants of 'Unique Light Red' are scarlet red in color.
3. Plants of the new *Calibrachoa* have good garden performance whereas plants of 'Unique Light Red' have poor garden performance.

Plants of the new *Calibrachoa* can be compared to plants of the *Calibrachoa* sp. 'USCALI11', disclosed in U.S. Plant Pat. No. 14,968. In side-by-side comparisons, plants of the new *Calibrachoa* differ primarily from plants of 'USCALI11' in the following characteristics:

1. Plants of the new *Calibrachoa* are more mounding than and not as upright as plants of 'USCALI11'.
2. Plants of the new *Calibrachoa* and 'USCALI11' differ in flower color as flowers of plants of the new *Calibrachoa* are dark red in color whereas flowers of plants of 'USCALI11' are light red purple in color.

Plants of the new *Calibrachoa* can also be compared to plants of the *Calibrachoa* sp. 'USCALI51', disclosed in U.S. Plant Pat. No. 14,874. In side-by-side comparisons, plants of the new *Calibrachoa* differ primarily from plants of 'USCALI51' in the following characteristics:

1. Plants of the new *Calibrachoa* are more mounding than and not as upright as plants of 'USCALI51'.
2. Plants of the new *Calibrachoa* and 'USCALI51' differ in flower color as flowers of plants of the new *Calibrachoa* are dark red in color whereas flowers of plants of 'USCALI51' are violet in color.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

At the top of the photographic sheet (FIG. 1) is a side perspective view of a typical flowering plant of 'BBCAL83901' grown in a container and at the bottom of the photographic sheet is a close-up view of a typical flowering plant of 'BBCAL83901'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Calibrachoa* production. During the production of the plants, day temperatures averaged 27° C. and night temperatures averaged 15° C. Plants were pinched three weeks after planting and were ten weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calibrachoa* sp. 'BBCAL83901'.

Parentage:

*Female, or seed, parent.*—Proprietary seedling selection of *Calibrachoa* sp. identified as code number 15CB354-01, not patented.

*Male, or pollen, parent.*—*Calibrachoa* sp. 'Unique Light Red', not patented.

Propagation:

*Type.*—By vegetative terminal cuttings.

*Time to initiate roots, summer.*—About five to seven days at ambient temperatures ranging from 17° C. to 29° C.

*Time to initiate roots, winter.*—About seven to ten days at ambient temperatures ranging from 17° C. to 21° C.

*Time to produce a rooted plant, summer.*—About four to five weeks at ambient temperatures ranging from 17° C. to 29° C.

*Time to produce a rooted plant, winter.*—About five to six weeks at ambient temperatures ranging from 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, upright to outwardly spreading and mounding plant habit; moderately vigorous growth habit and moderate growth rate; freely branching habit with about four primary lateral branches each with about eight secondary branches developing per plant; dense and bushy appearance.

*Plant height.*—About 10 cm.

*Plant diameter.*—About 21.9 cm.

Lateral branch description:

*Primary branches.*—Length: About 14.7 cm. Diameter: About 2.9 mm. Internode length: About 1 cm.

*Secondary branches.*—Length: About 9.2 cm. Diameter: About 1.8 mm. Internode length: About 7 mm.

*Strength.*—Moderately strong, flexible and sturdy.

*Aspect.*—Semi-upright to horizontal.

*Texture and luster.*—Densely pubescent; matte.

*Color, developing.*—Close to 145B.

*Color, developed.*—Close to 145A.

Leaf description:

*Arrangement*.—Before flowering, alternate; after flowering, opposite; leaves simple.

*Length*.—About 3.6 cm.

*Width*.—About 9 mm.

*Shape*.—Elliptic.

*Apex*.—Acute.

*Base*.—Attenuate.

*Margin*.—Entire.

*Texture and luster, upper surface*.—Sparsely pubescence; slightly glossy.

*Texture and luster, lower surface*.—Sparsely pubescence; matte.

*Venation pattern*.—Pinnate; arcuate.

*Color*.—Developing leaves, upper surface: Close to N137B. Developing leaves, lower surface: Close to 145B. Fully expanded leaves, upper surface: Close to N137B; venation, close to 145B. Fully expanded leaves, lower surface: Close to 147B; venation, close to 145C.

*Petioles*.—Length: About 7.4 mm. Diameter: About 2 mm. Strength: Moderately strong, flexible. Texture and luster, upper and lower surfaces: Sparsely pubescent; matte. Color, upper surface: Close to 145B. Color, lower surface: Close to 145C.

Flower description:

*Flower type and flowering habit*.—Single salverform flowers arising from leaf axils; freely flowering habit with typically about 164 flowers and flower buds developing per plant at one time; flowers face upright to outwardly.

*Fragrance*.—None detected.

*Natural flowering season*.—Plants of the new *Calibrachoa* begin flowering about six to eight weeks after planting; plants flower continuously from the spring though the summer until frost.

*Flower longevity*.—Individual flowers last about seven to ten days on the plant; flowers not persistent.

*Flower buds*.—Length: About 1.8 cm. Diameter: About 6.5 mm. Shape: Oblong, elongate. Texture and luster: Moderately pubescence; matte. Color: Close to N77B.

*Flower diameter*.—About 3 cm.

*Flower length* (*height*).—About 1.7 cm.

*Flower throat diameter*.—About 8 mm.

*Flower tube length*.—About 1.4 cm.

*Flower tube diameter*.—About 8 mm.

*Corolla*.—Arrangement: Five fused petals opening into a flared trumpet. Petal lobe length (from throat): About 1.5 cm. Petal lobe width: About 1.5 cm. Petal shape: Spatulate. Petal apex: Obtuse to slightly emarginate. Petal margin: Entire; slightly undulate. Petal texture and luster, upper surface: Smooth, glabrous, velvety; matte. Petal texture and luster, lower surface: Sparsely to moderately pubescent; matte. Throat texture and luster: Smooth, glabrous; matte. Tube texture and luster: Moderately pubescent; matte. Color: Petal lobe, when opening, upper surface: Close to N57A. Petal lobe, when opening, lower surface: Close to 59D. Petal lobe, fully opened, upper surface: Close to 53D; towards the base, close to 46B; venation, close to 46B; color becoming closer to 52A to 52B with development. Petal lobe, fully opened, lower surface: Close to 59D; midvein, close to N77A and lateral venation, close to 58A; color becoming closer to 54B with development. Throat: Close to 12A; narrow ring at the transition between throat and petal lobe, close to 178A; venation, close to 200A. Tube: Darker than 7D; venation, close to 200A.

*Calyx*.—Arrangement: One star-shaped calyx tube with five sepals fused towards the base and arranged in a single whorl; sepals flaring outwardly and reflexing towards the apex. Length: About 1.2 cm. Diameter: About 1.4 cm. Sepal length: About 1.2 cm. Sepal width: About 2.5 mm. Sepal shape: Lanceolate. Sepal apex: Acute. Sepal margin: Entire. Sepal texture and luster, upper surface: Moderately pubescent; matte. Sepal texture and luster, lower surface: Sparsely pubescent; matte. Sepal color, upper surface: Close to 137B. Sepal color, lower surface: Close to 137C.

*Peduncles*.—Length: About 1.8 cm. Diameter: About 1 mm. Angle: About 45° to 90° from stem axis. Strength: Moderately strong, wiry and flexible. Texture and luster: Densely pubescent; matte. Color: Close to 145B.

*Reproductive organs*.—Stamens: Quantity: Five per flower. Filament length: About 9 mm. Filament color: Close to 154C. Anther length: About 0.9 mm. Anther shape: Ellipsoidal. Anther color: Close to 10C. Pollen amount: Abundant. Pollen color: Close to 11B. Pistils: Quantity: One per flower. Pistil length: About 8 mm. Style length: About 7 mm. Style color: Close to 145B. Stigma diameter: About 0.9 mm. Stigma shape: Ellipsoidal. Stigma color: Close to 145A. Ovary color: Close to 145B.

*Seeds and fruits*.—To date, seed and fruit development have not been observed on plants of the new *Calibrachoa*.

Garden performance: Plants of the new *Calibrachoa* have been observed to have good garden performance and tolerate wind, rain and to be suitable for USDA Hardiness Zones 9 to 11.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'BBCAL83901' as illustrated and described.

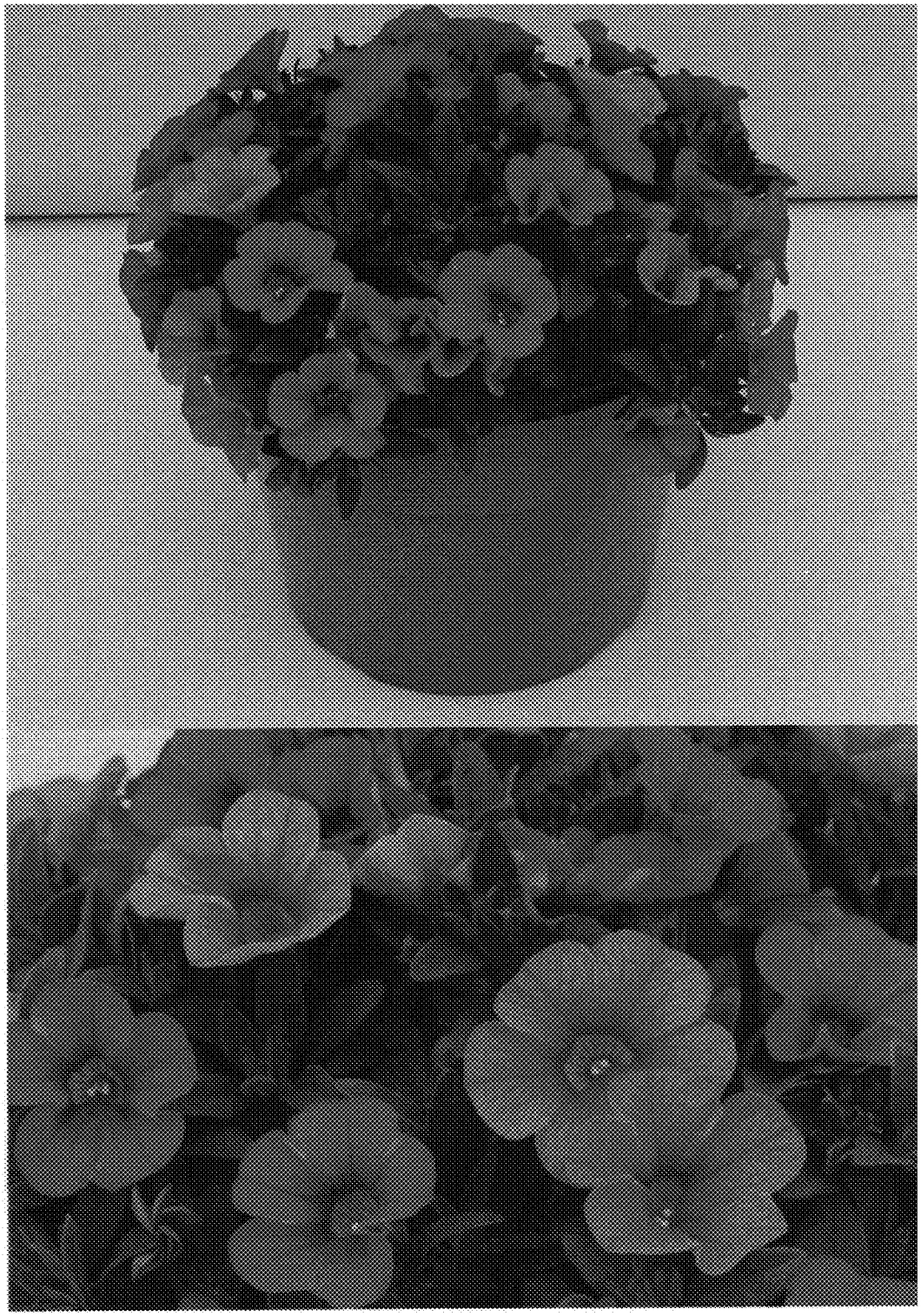

* * * * *